United States Patent [19]

Titus et al.

[11] Patent Number: 4,537,893

[45] Date of Patent: Aug. 27, 1985

[54] OCTAHYDROTHIAZOLO[4,5-G]QUINOLINES AND USE AS PROLACTIN SECRETION INHIBITORS

[75] Inventors: Robert D. Titus; Edmund C. Kornfeld, both of Indianapolis, Ind.

[73] Assignee: Eli Lilly and Company, Indianapolis, Ind.

[21] Appl. No.: 604,687

[22] Filed: Apr. 27, 1984

[51] Int. Cl.$^3$ .................... A61K 31/47; C07D 513/02
[52] U.S. Cl. .................................. 514/293; 546/83; 546/84; 546/164
[58] Field of Search .................... 546/83, 84, 164; 424/258

[56] References Cited

U.S. PATENT DOCUMENTS

| | | | |
|---|---|---|---|
| 3,714,170 | 1/1973 | Dohmori et al. | 546/83 |
| 4,258,049 | 3/1981 | Bondinell et al. | 546/83 |
| 4,367,231 | 1/1983 | Kornfeld et al. | 546/82 |

OTHER PUBLICATIONS

Fujita et al., *J. Pharm. Soc. Japan*, 76, 817–820, (1956).

*Primary Examiner*—Henry R. Jiles
*Assistant Examiner*—Ann Bucci
*Attorney, Agent, or Firm*—James L. Rowe; Arthur R. Whale

[57] ABSTRACT

Trans-($\pm$) 2 and/or 5-permissibly substituted octahydrothiazolo[4,5-g]quinolines and acid addition or quaternary salts thereof and, individual enantiomers thereof, useful as dopamine agonists.

53 Claims, No Drawings

OCTAHYDROTHIAZOLO[4,5-G]QUINOLINES AND USE AS PROLACTIN SECRETION INHIBITORS

SUMMARY OF THE INVENTION

This invention provides trans(±)-2-permissibly-substituted-5-alkyl-4,4a,5,6,7,8,8a,9-octahydrothiazolo[4,5-g]quinolines of the structure

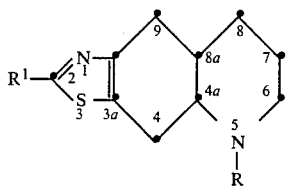

I wherein R is H, methyl, ethyl, allyl or n-propyl, $R^1$ is H, OH, halogen, methyl, $NH_2$, $NHC_{1-3}$alkyl, $N(C_{1-3}$ alkyl$)_2$, 1-pyrrolidinyl, $NHCOC_{1-3}$alkyl, or $NHC_{1-2}$alkylphenyl, and pharmaceutically-acceptable acid addition salts, thereof.

Also falling within the ambit of this invention are quaternary $C_{1-3}$ alkyl halide salts of compounds according to I above when $R^1$ is H and R has its previous meaning. Such quaternary salts include the methiodide, ethiodide, methylchloride, n-propylbromide and the like salts.

While the compounds represented by I except when R is H, are active drugs; i.e., dopamine agonists, several are also useful intermediates; for example, compounds in which $R^1$ is $NH_2$ can be acylated to yield compounds in which $R^1$ is $NHCOC_{1-3}$ alkyl or a compound in which $R^1$ is H can be treated with a $C_{1-3}$ alkyl iodide, for example, to yield a quaternary salt. Compounds in which R is H are intermediates in that they can, in general, be alkylated to yield derivatives in which R is methyl, ethyl or n-propyl.

Compounds, according to I in which $R^1$ is halogen; i.e., trans-(±)-2-bromo-5-$C_{1-3}$ straight chain alkyl (or allyl)-4,4a,5,6,7,8,8a,9-octahydrothiazolo[4,5-g]quinolines, which shows D-2 dopamine agonist activity, are also useful intermediates for preparing certain of the 2-substituted derivatives described by I.

As previously stated, compounds according to I are dopamine D-2 agonists, manifesting their activities in tests designed to demonstrate utility as prolactin secretion inhibitors, in treatment of Parkinson's Disease, in treating sexual dysfunction, anxiety or depression or as hypotensive agents.

In the above formula, when $R^1$ is OH, the compound is the enolic form of II

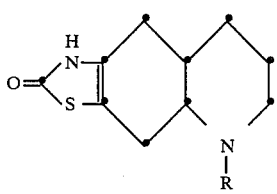

II named as trans-(±)-5-straight chain $C_{1-3}$alkyl or allyl4-,4a,5,6,7,8,8a,9-octahydrothiazolo[4,5-g]quinolin2(1H)-one.

In the above formula, the term "$C_{1-3}$ alkyl" includes methyl, ethyl, n-propyl and isopropyl while the term "straight-chain $C_{1-3}$ alkyl" includes only the first three radicals. The term "halogen" means members of the 7th main group of the Periodic Table, preferably chlorine and bromine.

Pharmaceutically-acceptable acid addition salts of the compounds of this invention include salts derived from non-toxic inorganic acids such as: hydrochloric acid, nitric acid, phosphoric acid, sulfuric acid, hydrobromic acid, hydriodic acid, phosphorous acid and the like, as well as salts derived from non-toxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and the like salts.

Compounds according to I above have two asymmetric carbons (optical centers) at 4a and 8a and can thus exist as four stereoisomers occurring as two racemic pairs, ordinarily designated as the trans-(±) racemate and the cis-(±) racemate. The trans racemate (I) of this invention is composed of the trans-(−) stereoisomer (4aR,8aR stereoisomer) represented by III below and the trans-(+)(4aS,8aS) stereoisomer represented by IIIa.

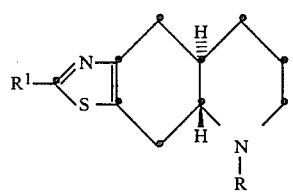

III

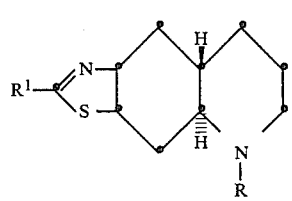

IIIa wherein R and $R^1$ have their previously assigned meanings. The trans-(−)-(4aR,8aR) stereoisomers represented by III wherein R is other than H and $R^1$ is other than halogen are the active dopamine D-2 agonist component of the racemate (I) and are preferred over the trans-(+)-stereoisomers. However, the corresponding trans-(+)-stereoisomers (IIIa) have dopamine D-1 agonist activity.

The trans-(−) enantiomers according to III thus form a second and preferred aspect of this invention. Intermediates, such as the 4aR,8aR-2-bromo-5-$C_{1-3}$ straight-chain alkyl (or allyl)-4,4a,5,6,7,8,8a,9-octahydrothiazolo[4,5-g]quinolines or compounds according to III or IIIa in which R is H are also optically active compounds falling within the scope of this invention.

As dopamine D-2 agonists, compounds represented by III above in which R is other than H and R' is other than halogen may be employed as drugs either as the free base or as a pharmaceutically-acceptable acid addition salt thereof.

A preferred group of drugs according to III are those in which (1) R is n-propyl
(2) $R^1$ is $NH_2$
(3) $R^1$ is $NHCH_3$
(4) $R^1$ is H
(5) $R^1$ is $N(CH_3)_2$
(6) $R^1$ is $NH—CO—CH_3$ Compounds of this invention include, illustratively, Trans-($\pm$)-2-amino-5-ethyl-4,4a,5,6,7,8,8a,9-octahydrothiazolo[4,5-g]quinoline maleate, Trans-($\pm$)-2-n-propylamino-5-n-propyl-4,4a,5,6,7,8,8a,9-octahydrothiazolo[4,5-g]quinoline sulfate, Trans-($\pm$)-5-ethyl-4,4a,5,6,7,8,8a,9-octahydrothiazolo[4,5-g]quinoline ethiodide, Trans-($\pm$)-2-dimethylamino-5-n-propyl-4,4a,5,6,7,8,8a,9,-octahydrothiazolo[4,5-g]quinoline dihydrobromide, 4aR,8aR-2-methylethylamino-5-ethyl-4,4a,5,6,7,8,8a,9-octahydrothiazolo[4,5-g]quinoline succinate, 4aR,8aR-2-amino-5-methyl-4,4a,5,6,7,8,8a,9-octahydrothiazolo[4,5-g]quinoline dihydrochloride, Trans-($\pm$)-2-phenethylamino-5-n-propyl-4,4a,5,6,7,8,8a,9-octahydrothiazolo[4,5-g]quinoline tartrate, 4aR,8aR-2-benzylamino-5-ethyl-4,4a,5,6,7,8,8a,9-octahydrothiazolo[4,5-g]quinoline phosphate, 4aR,8aR-2-acetylamino-5-methyl-4,4a,5,6,7,8,8a,9-octahydrothiazolo-[4,5-g]quinoline terephthalate, trans-($\pm$)-2-propionylamino-5-ethyl-4,4a,5,6,7,8,8a,9-octahydrothiazolo[4,5-g]quinoline dinitrobenzoate, Trans-($\pm$)-2-chloro-5-n-propyl-4,4a,5,6,7,8,8a,9-octahydrothiazolo[4,5-g]quinoline methanesulfonate (mesylate), Trans-($\pm$)-2-bromo-5-n-propyl-4,4a,5,6,7,8,8a,9-octahydrothiazolo[4,5-g]quinoline p-toluene sulfonate (p-tosylate) and the like.

Compounds represented by Formula III, as dopamine (D-2) agonists, are substantially devoid of other agonist or antagonist (blocking) activities. As D-2 dopamine agonists, the compounds are useful in treating Parkinson's Syndrome, in treating sexual dysfunction, as antidepressants or as anti-anxiety agents, in lowering blood pressure in hypertensive mammals and in inhibiting prolactin secretion. Thus, other embodiments of this invention include the treatment, by the racemates (I) or the trans-($-$) enantiomers, of hypertension, of depression, of anxiety, of Parkinson's disease and of disease states characterized by an excess of prolactin secretion such as galactorrhea and inappropriate lactation.

A still further embodiment of this invention is the provision of pharmaceutical formulations for administering drugs according to I or III in the treatment methods outlined above.

The 4aS,8aS enantiomers—formula IIIa—have, as previously stated, D-1 dopamine agonist activity. However, this activity is manifested at higher dosage levels than those necessary to achieve D-2 dopamine agonist activity by the enantiomers of formula III. Thus, the trans-($\pm$) racemates represented by I can be used as D-2 agonists without substantial D-1 activity. The racemates are also useful as a source of the individual enantiomers.

Racemic compounds of this invention when, in Formula I, $R^1$ is $NH_2$, $NH(C_{1-3}$ alkyl), $N(C_{1-3}$ alkyl)$_2$, or $NH(C_{1-2}$ phenyl), are readily synthesized according to the following reaction scheme:

Synthetic Route I

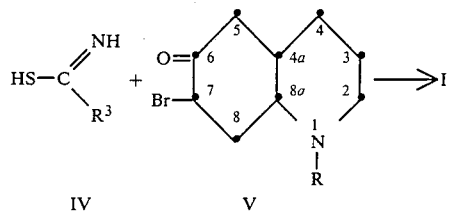

wherein R has its previous meaning, $R^3$ is $NH_2$, $NH(C_{1-3}$ alkyl), $NH(C_{1-2}$ alkylphenyl) or $N(C_{1-3}$ alkyl)$_2$ and the 4a,8a ring fusion is trans. Formula IV above represents an isothiourea tautomeric with the corresponding thiourea; i.e., if $R^3$ is $NH_2$, the compound becomes

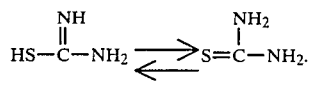

The other starting material (V) is prepared by brominating an N-$C_{1-3}$ straight-chain alkyl-6-oxodecahydroquinoline. These latter compounds can be prepared by the method of Schaus, Ser. No. 384,817, filed June 2, 1982, whereby a 6-alkoxyquinoline of formula VI

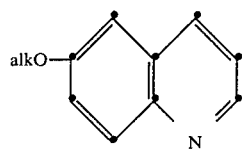

wherein alk is lower alkyl, is quaternized with a $C_{1-3}$ straight-chain alkyl halide ($R^4X$) and the quaternized salt hydrogenated to yield an N-$C_{1-3}$ straight-chain alkyl-6-alkoxy-1,2,3,4-tetrahydroquinoline of formula VII

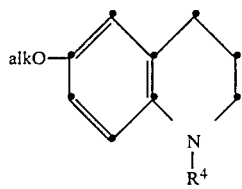

wherein $R^4$ is $C_{1-3}$ straight-chain alkyl. The particular $C_{1-3}$ alkyl group ($R^4$) remains intact through the next two reduction steps: a Birch reduction followed by a sodium cyanoborohydride (or borohydride) reduction to yield, ultimately, an octahydroquinoline of the formula VIII

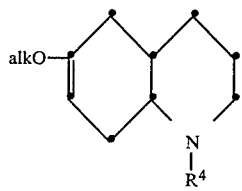

wherein $R^4$ is $C_{1-3}$ straight-chain alkyl, alk has its previous meaning, and the ring junction hydrogens are trans.

This enol ether, upon treatment with acid, yields the N-substituted decahydroquinoline-6-one (IX)

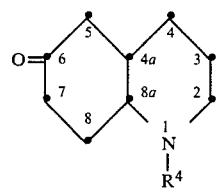

in which the 4a,8a ring junction is transfused and the N-substituent ($R^4$) is $C_{1-3}$ straight-chain alkyl.

Bromination of IX at C-7 using, for example, hydrogen bromide and bromine in glacial acetic acid and UV light, yields V, one starting material of Synthetic Route I.

An alternate preparation of the trans-(±)-1-$C_{1-3}$ straight-chain alkyl-6-oxodecahydroquinoline (IX) is disclosed in U.S. Pat. No. 4,198,415 Cols. 4–5 (where it is compound number VII in the Reaction Scheme).

An additional procedure for preparing IX has been developed by Weigel following the procedure of Evans et al. *J.A.C.S.*, 7593 (1970). Here the ring closure reaction yields a 1-$C_{1-3}$ straight-chain alkyl-6-oxo-1,2,3,4,5,6,7,8-octahydroquinoline. Reduction of the 4a,8a double bond with $NaBH_4$ at a temperature above 25° C. yields a trans-(±)-1-$C_{1-3}$ straight chain alkyl-6-hydroxydecahydroquinoline, which type of compound can be oxidized to the corresponding 6-oxo derivative by standard procedures. Alternatively, the ketone group of the 6-oxo-octahydroquinoline can be protected, as by ketal formation, and the $NaBH_4$ reduction to yield the trans-(±) derivative carried out on the ketal. Acid treatment of the reduced ketal yields the desired 6-oxo derivative (IX).

The optically-active octahydrothiazolo[4,5g]quinoline of formulas III and IIIa can be prepared by resolution of the trans-(±) racemates represented by I above. A preferred procedure, however, is to resolve the trans-(±) ketone (IX) using the procedure of Schaus and Booher, Ser. No. 439,107 filed Nov. 1, 1982. The 4aR,-8aR enantiomer thus prepared, IXa,

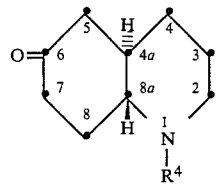

wherein $R^4$ has its previous meaning can then be substituted for the racemic ketone IX in Synthetic Route I; i.e., bromination of IXa yields a 4aR,8aR-1-$C_{1-3}$ straight-chain alkyl-6-oxo-7-bromodecahydroquinoline (Va—V in which the bridgehead hydrogens are 4aR,-8aR) which derivative then reacts with an isothiourea (IV) to yield compounds according to III in which $R^1$ is $R^4$, and R is $C_1$-$C_3$ straight-chain alkyl.

The D-1 agonists of this invention (IIIa) are prepared in analogous fashion from 4aS,8aS-1-$C_{1-3}$ straight-chain alkyl-6-oxodecahydroquinoline, which is in turn obtained by resolution of the trans-(±)racemate.

Those drugs of this invention in which $R^1$ is $NH(C_{1-3}$ alkyl-CO) in I, III or IIIa are prepared by acylating the corresponding compound in which $R^1$ is $NH_2$. Compounds according to I, III, or IIIa in which $R^1$ is H are prepared by diazotizing the primary amine group at C-2 (I, III or IIIa where $R^1$ is $NH_2$) and treating the diazonium salt with hypophosphorous acid. Alternatively, a 1-substituted-6-oxo-7-bromodecahydroquinoline (V or an enantiomer thereof) can be reacted with a thioamide of the formula ($R^6$—CS—$NH_2$ where $R^6$ is H or $CH_3$) in acetonitrile or other suitable non-reacting mutual solvent, to yield those compounds according to I, III or IIIa in which $R^1$=H or methyl. The thioamide can be prepared in situ from $P_2S_5$ and formamide or acetamide, or the thioamides can be obtained commercially in the case of thioacetamide.

The quaternary salts of this invention are prepared by quaternizing those compounds wherein $R^1$ is H (in I, III or IIIa) with a $C_{1-3}$ alkyl halide or the like.

Treatment of the above diazonium salt (I, III or IIIa wherein $R^1$ would be $N_2^+$ $X^-$ where X is a suitable anion—phosphate, sulfate or the like) with HBr or HCl produces those compounds of this invention (I, III or IIIa) wherein $R^1$ is Cl or Br.

Those compounds according to I, III or IIIa wherein $R^1$ is OH—tautomeric with the 2-oxo derivatives II—or the corresponding 4aR,8aR or 4aS,8aS derivatives are prepared by hydrolysing a 2-bromo or 2-chloro compound.

Those compounds according to I, III or IIIa in which $R^1$ is 1-pyrrolidinyl are prepared by reacting the corresponding 2-bromo or 2-chloro compound with pyrrolidine.

Finally, compounds according to I, III or IIIa in which R is allyl are prepared by starting with a 6-oxodecahydroquinoline (X) according to Synthetic Route II below.

Synthetic Route II

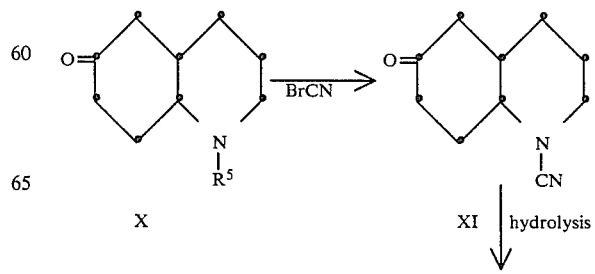

-continued
Synthetic Route II

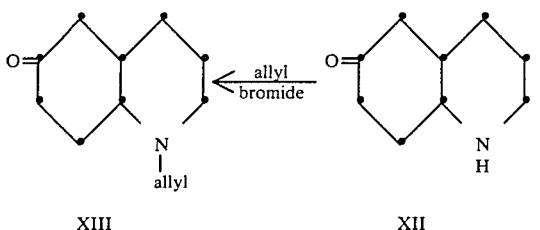

where $R^5$ is lower alkyl or benzyl. The N-allyl product XIII can be brominated to yield V in which R is allyl in Synthetic Route I, being careful not to brominate the N-allyl group in producing this compound. Alternatively, a compound according to X wherein $R^5$ is benzyl and the 6-oxo group is protected by ketal formation can be hydrogenated so as to hydrogenolyze the benzyl group to form a secondary amine. Removal of the ketal protecting group with acid yields XIII. The above procedures are outlined in the copending application of Titus and Bach, Ser. No. 535,522 filed 9-26-83.

This invention is further illustrated by the following specific examples.

EXAMPLE 1

Preparation of Trans-(±)-2-amino-5-n-propyl-4,4a,5,6,7,8,8a-9-octahydrothiazolo[4,5-g]quinoline Five grams of trans-(±)-1-n-propyl-6-oxodecahydroquinoline were dissolved in 30 ml. of glacial acetic acid. Five and eight tenths milliliters of 37% by weight hydrogen bromide in glacial acetic acid were added followed by the dropwise additions of 1.5 ml. of bromine dissolved in glacial acetic acid. The reaction mixture was illuminated with ultraviolet radiation using a commercially available sunlamp. The illuminated reaction mixture was stirred for one-half hour after all the reactants had been added. Volatile constituents were removed from the reaction mixture in vacuo yielding, as a residue, trans-(±)-1-n-propyl-6-oxo-7-bromodecahydroquinoline hydrobromide. One hundredth mole of this salt was dissolved in 50 ml. of ethanol. Eighty-four hundredths grams of thiourea were added thereto. The resulting mixture was refluxed for about 18 hours under a nitrogen blanket. A colorless solid began to form after about 20 minutes. The reaction mixture was cooled to about 0° C. and the solid, which had continued to form, was separated by filtration. The filter cake was dried in vacuo. One and fifteen hundredths grams of trans-(±)-2-amino-5-n-propyl-4,4a,5,6,7,8,8a,9-octahydrothiazolo[4,5-g]quinoline dihydrobromide salt were obtained. The salt melted above 255° C., tlc (9:1 chloroform:methanol plus a trace of ammonium hydroxide) $R_f$=0.13.

Analysis Calculated: C, 38.02; H, 5.33; N, 10.30; S, 7.78. Found: C, 37.79; H, 5.61; N, 10.17; S, 7.76.

The dihydrobromide salt prepared as above was converted to the free base by standard procedures using aqueous ammonium hydroxide. The free base thus obtained crystallized; m.p.=184°-185° C. with decomposition. One hundred fifty milligrams of the free base were dissolved in methanol. Two and ninety-eight hundredths milliliters of 0.2M aqueous hydrochloric acid (one equivalent) were added and the resulting mixture warmed on the steam bath. The volatile constituents were removed in vacuo and the residue, the hydrochloride salt of trans-(±)-2-amino-5-n-propyl-4,4a,5,6,7,8,8a,9-octahydrothiazolo[4,5-g]quinoline, melted above 240° C. after recrystallization from anhydrous ethanol.

Analysis Calculated: C, 54.24; H, 7.70; N, 14.60; Cl, 12.32. Found: C, 54.52; H, 7.91; N, 14.43; Cl, 12.56.

The dihydrochloride salt of trans-(±)-2-amino-5-n-propyl-4,4a,5,6,7,8,8a,9-octahydrothiazolo[4,5-g]quinoline was prepared by dissolving 1 g. of the free base in methanol, saturating the solution with gaseous hydrogen chloride and adding ether to the solution to the point of incipient precipitation. Cooling the crystallization mixture produced crystals which were separated by filtration. The filter cake was recrystallized first from an ether/ethanol solvent mixture and then from ethanol alone. Sixty-five hundredths grams of the dihydrochloride salt were recovered melting at 274° C. with decomposition.

Analysis Calculated: C, 48.14; H, 7.15; N, 12.96. Found: C, 48.29; H, 7.04; N, 12.85.

The above series of reactions was repeated using 4,aR,8aR-1-n-propyl-6-oxodecahydroquinoline as the starting material. The ketone was alpha brominated by the above procedure to yield 4aR,8aR-1-n-propyl-6-oxo-7-bromodecahydroquinoline hydrobromide which was in turn reacted with thiourea in anhydrous ethanol. Two and four tenths grams of a colorless solid dihydrobromide were obtained from 1.01 g. of thiourea. The dihydrobromide salt was dissolved in water and the free base isolated by treatment with aqueous ammonia; yield=1.5 g. The free base was transformed to the hydrochloride salt by the above procedures. One and eight hundredths grams of 4aR,8aR-2-amino-5-n-propyl-4,4a,5,6,7,8,8a,9-octahydrothiazolo[4,5-g]quinoline hydrochloride were obtained having the following physical characteristics.

tlc (9:1 $CHCl_3$/MeOH+tr. $NH_4OH$) $R_f$=0.58.

Mass spectrum:molecular ion at 251.

Melting point above 225° C. after recrystallization from ethanol.

$[\alpha]_D^{20}$ (water)=−140.4°; $[\alpha]_{365}^{20}$=−497.8°.

Analysis Calculated: C, 54.24; H, 7.70; N, 14.60. Found: C, 54.01; H, 7.86; N, 14.86.

EXAMPLE 2

Preparation of Trans-(±)-5-n-propyl-4,4a,5,6,7,8,8a,9-octahydrothiazolo[4,5-g]quinoline A solution of 0.24 g. of trans-(±)-2-amino-5-n-propyl-4,4a,5,6,7,8,8a,9-octahydrothiazolo[4,5-g]quinoline in 10 ml. of 85% phosphoric acid was cooled to about −8° C. A saturated solution of 1.17 g. of sodium nitrite in water was added below the surface of the phosphoric acid solution at such a rate as to keep the reaction temperature from going above about −4° C. The reaction mixture was then added in dropwise fashion to 10 ml. of 50% aqueous hypophosphorus acid kept at a temperature of about 0° C. This new reaction mixture was stirred until gas evolution had ceased, at which time it was poured over ice. The aqueous mixture was made strongly basic with aqueous ammonium hydroxide. The aqueous layer was extracted several times with chloroform. The chloroform extracts were combined, and the combined extracts washed, first with water and then with saturated aqueous sodium chloride, and then dried. Removal of the chloroform in vacuo yielded trans-(±)-5-n-propyl-4,4a,5,6,7,8,8a,9-octahydrothiazolo[4,5-g]quinoline free base having the following physical characteristics: tlc (9:1 $CHCl_3$/MeOH+Tr.$N_4OH$)$R_f$=0.70.

The free base was chromatographed over florisil using chloroform containing increasing amounts (0-3%) of methanol as the eluant. Fractions shown by tlc to contain the free base were combined and the solvents evaporated therefrom to yield a residue which was dissolved in ethanol. The ethanol solution was saturated with gaseous hydrogen chloride to yield trans-(±)-5-n-propyl-4,4a,5,6,7,8,8a,9-octahydrothiazolo[4,5-g]quinoline dihydrochloride; yield=0.1 g.; m.p.=above 240° C.

Analysis Calculated: C, 50.48; H, 7.17; N, 9.09. Found: C, 50.69; H, 6.87; N, 9.18.

Alternatively, the above compound can be prepared by the following procedure:

One and seven tenths grams of phosphorus pentasulfide were slurried in 5 ml. of p-dioxane. One and five tenths milliters of formamide were added and, when the reaction mixture began to exotherm, it was cooled in an ice/water bath. Next, 2.54 millimoles of trans-(±)-1-n-propyl-6-oxo-7-bromodecahydroquinoline hydrobromide in 10 ml. of acetonitrile were added in dropwise fashion and the resulting mixture heated to refluxing temperature for about one hour. Five milliliters of water plus 1 ml. of 12N aqueous hydrochloric acid were added and the reaction mixture heated for an additional hour, after which time it was cooled and the cooled reaction mixture diluted with water. The acidic reaction mixture was extracted with ether and the ether extract discarded. The acidic aqueous layer was then made basic with 10% aqueous sodium hydroxide and the basic layer extracted several times with equal volumes of chloroform. The chloroform extracts were combined and the chloroform removed by evaporation in vacuo. The residue, containing trans-(±)-5-n-propyl-4,4a,5,6,7,8,8a,9-octahydrothiazolo[4,5-g]quinoline formed in the above reaction, was chromatographed over florisil using chloroform containing increasing amounts (0-2%) of methanol as the eluant. Fractions shown to contain the desired product were combined, and the combined fractions rechromatographed to yield about 1.2 g. of a dark orange-red transparent oil. NMR indicated that the oil contained about 53% of the desired product. This oil was then rechromatographed over basic alumina using chloroform containing 2% methanol as the eluant. Fractions containing trans-(±)-5-n-propyl-4,4a,5,6,7,8,8a,9-octahydrothiazolo[4,5-g]quinoline were combined, and the solvent evaporated therefrom. The product thus obtained had identical properties with that previously found, including mass spectrum, M+ =236.

The methiodide salt of trans-(±)-5-n-propyl-4,4a,5,6,7,8,8a,9-octahydrothiazolo[4,5-g]quinoline was prepared from 0.22 g. of the free base in acetonitrile to which was added 15 ml. of methyliodide. The reaction mixture was refluxed overnight and then cooled to room temperature. The solid which had formed, comprising trans-(±)-5-n-propyl-4,4a,5,6,7,8,8a,9-octahydrothiazolo[4,5-g]quinolinium methiodide hydroiodide formed in the above reaction, was separated by filtration and the filter cake dried; yield=0.2 g.; melting point=above 225° C.; mass spectrum, M+ =251.

Analysis Calculated: C, 33.22; H, 4.78; N, 5.53 Found: C, 33.42; H, 4.57; N, 5.50

EXAMPLE 3

Preparation of Trans-(±)-2-bromo-5-n-propyl-4,4a,5,6,7,8,8a,9-octahydrothiazolo[4,5-g]quinoline Four and thirteen hundredths grams of trans-(±)-2-amino-5-n-propyl-4,4a,5,6,7,8,8a,9-octahydrothiazolo[4,5-g]quinoline dihydrobromide were dissolved in 30 ml. of 85% phosphoric acid and the solution cooled to about −10° C. Nine milliliters of nitric acid were added followed by 1.72 g of sodium nitrite in water added in dropwise fashion via a syringe placed below the surface of the solution. The nitrite solution was added at such a rate as to keep the temperature below about −5° C. After the addition had been completed, the reaction mixture was stirred for an additional half hour in the range −5°-0° C. This solution was added with vigorous stirring to a mixture of 3 g. of copper powder in 50 ml. of 48% aqueous hydrobromic acid cooled to −5° C. The reaction mixture was stirred for about 15 minutes at −5° C. during which time a vigorous evolution of gas ensued. The reaction mixture was next slurried with ice, and the resulting mixture made basic with concentrated aqueous ammonium hydroxide. The aqueous alkaline layer was extracted several times with equal volumes of chloroform. The chloroform extracts were combined and the combined extracts washed successively with water and with saturated aqueous sodium chloride. The combined extracts were then dried, and the solvent removed therefrom in vacuo. TLC using the system of Example 1 gave two major spots ($R_f$=0.72 and 0.57). The residues obtained above were therefore chromatographed over florisil using chloroform as the eluant. Compounds corresponding to the two spots appearing on TLC were separated by this chromatographic procedure. Fractions containing the faster moving compound were combined, and the solvent removed therefrom in vacuo. The resulting residue was dissolved in methanol, and the monohydrochloride salt prepared by the procedure of Example 1. Five tenths grams of trans-(±)-2-bromo-5-n-propyl-4,4a,5,6,7,8,8a,9-octahydrothiazolo[4,5-g]quinoline hydrochloride melting above 235° C. were obtained.

Analysis Calculated: C, 44.39; H, 5.73; N, 7.96; Br, 22.72; Cl, 10.08. Found: C, 44.40; H, 5.69; N, 7.84; Br, 22.50; Cl, 9.98.

The second product obtained in similar fashion—weight=0.70 g.—was shown to be trans-(±)-5-n-propyl-4,4a,5,6,7,8,8a,9-octahydrothiazolo[4,5-g]quinoline hydrochloride (no substituent at C-2), a compound which had been previously prepared.

The above procedure was repeated with 2.5 g. of starting material, except that the diazotization mixture was added to 2 g. of cupric sulfate pentahydrate and 5.5 g. of sodium bromide in 10 ml. of water. The product obtained after purification showed essentially one spot on TLC. Total yield=1.7 g. of trans-(±)-2-bromo-5-n-propyl-4,4a,5,6,7,8,8a,9-octahydrothiazolo[4,5-g]quinoline free base.

EXAMPLE 4

Preparation of Trans-(±)-5-n-propyl-4,4a,5,6,7,8,8a,9-octahydrothiazolo[4,5-g]quinolin-2(1H)-one About 1.9 millimoles of trans-(±)-2-bromo-5-n-propyl-4,4a,5,6,7,8,8a,9-octahydrothiazolo[4,5-g]quinoline were dissolved in 10 ml. of 20% aqueous sulfuric acid. The solution was heated at about 100° C. for about five hours and then was cooled. The cooled solution was allowed to remain at ambient temperature for an additional 48 hours. The reaction mixture was then made basic with concentrated aqueous ammonium hydroxide. The aqueous mixture was extracted several times with equal volumes of chloroform. The chloroform extracts were combined, and the combined extracts washed with saturated aqueous sodium chloride and then dried. Evaporation of the chloroform in vacuo yielded trans-(±)-5-n-propyl-4,4a,5,6,7,8,8a,9-octahydrothiazolo[4,5-g]quinolin-2(1H)-one which was one spot material by TLC (9:1 CHCl$_3$/MeOH+trace NH$_4$OH); R$_f$=0.37. The compound showed a strong band at 1650 cm$^{-1}$ in the infrared indicating a carbonyl.

The residue was dissolved in methanol and the methanolic solution saturated with gaseous hydrogen chloride. The solvent was removed in vacuo and the residue crystallized from ethanol. Trans-(±)-5-n-propyl-4,4a,5,6,7,8,8a,9-octahydrothiazolo[4,5-g]quinolin-2(1H)-one hydrochloride thus prepared melted at about 250° C. after recrystallization from a methanol/ether solvent mixture; yield=0.18 g.

Analysis Calculated: C, 54.06; H, 7.33; N, 9.70. Found: C, 54.29; H, 7.25; N, 9.63.

EXAMPLE 5

Preparation of Trans-(±)-2-(1-pyrrolidinyl)-5-n-propyl-4,4a,5,6,7,8,8a,9-octahydrothiazolo[4,5-g]quinoline A reaction mixture, prepared from 6.6 g. of trans-(±)-2-bromo-5-n-propyl-4,4a,5,6,7,8,8a,9-octahydrothiazolo[4,5-g]quinoline and 20 ml. of pyrrolidine, was heated to reflux temperature for about 18 hours and was then cooled. The volatile constituents were removed in vacuo and the resulting residue diluted with water. The aqueous mixture was made strongly basic with concentrated aqueous ammonium hydroxide. The alkaline layer was extracted several times with equal volumes of chloroform. The chloroform extracts were combined, and the combined extracts washed with water and with saturated aqueous sodium chloride and were then dried. The solvent was evaporated therefrom in vacuo. TLC (9:1 CHCl$_3$/MeOH+a trace of aqueous ammonium hydroxide) showed one spot, more polar than starting material. The residue was therefore dissolved in chloroform and the chloroform solution chromatographed over a florisil column using chloroform as the eluant. Seventeen hundredths grams of a light yellow glass were obtained by this procedure. The glass was dissolved in ether and 0.06 g. of maleic acid in ethereal solution added thereto. A solid maleate salt precipitated. The ether was removed by decantation and the solid salt recrystallized from a mixture of ethanol and ether. Five hundredths grams of trans-(±)-2-(1-pyrrolidinyl)-5-n-propyl-4,4a,5,6,7,8,8a,9-octahydrothiazolo[4,5-g]quinoline maleate were obtained melting with decomposition at 184° C.

Mass spectrum: 305 (M+).

EXAMPLE 6

Preparation of Trans-(±)-2-acetylamino-5-n-propyl-4,4a,5,6,7,8,8a,9-octahydrothiazolo[4,5-g]quinoline A solution was prepared from 0.15 g. of trans-(±)-2-amino-5-n-propyl-4,4a,5,6,7,8,8a,9-octahydrothiazolo[4,5-g]quinoline (from Example 1) in 3 ml. of tetrahydrofuran (THF) to which has been added two drops of dimethylformamide (DMF). Five hundredths milliliters of acetyl chloride were added and the solution stirred at room temperature for 15 minutes. In time, the reaction mixture became a solid colorless mass. The solid was suspended in ether and the ethereal suspension filtered. The solid was then recrystallized from a methanol/ether solvent mixture to give purified trans-(±)-2-acetylamino-5-n-propyl-4,4a,5,6,7,8,8a,9-octahydrothiazolo[4,5-g]quinoline hydrochloride; yield=30.3%; melting point above 200° C.

Analysis Calculated: C, 54.61; H, 7.33; N, 12.74. Found: C, 54.39; H, 7.08; N, 12.74.

EXAMPLE 7

Preparation of Trans-(±)-2-methylamino-5-n-propyl-4,4a,5,6,7,8,8a,9-octahydrothiazolo[4,5-g]quinoline Following the procedure of Example 1, trans-(±)-1-n-propyl-6-oxo-7-bromodecahydroquinoline was reacted with N-methylthiourea in ethanol. The reaction mixture was heated to reflux temperature. A solid began to appear after about five hours of refluxing. Heating of the reaction mixture to reflux was continued for about 18 hours. The reaction mixture was then cooled to ambient temperature. The colorless solid which precipitated was separated by filtration and the filter cake was dried. The filter cake was dissolved in water and excess aqueous ammonium hydroxide was added to the solution. The alkaline solution was extracted with chloroform. The chloroform extract was separated, and the chloroform removed in vacuo to yield 1.14 g. (from 0.01 mole of starting material) of trans-(±)-2-methylamino-5-n-propyl-4,4a,5,6,7,8,8a,9-octahydrothiazolo[4,5-quinoline. The compound chromatographed over florisil using chloroform containing increasing amounts (0–5%) of methanol as the eluant. Fractions containing the more rapidly moving material were collected to yield 0.7 g. of a colorless solid. The solid was dissolved in methanol, and the methanol solution saturated with gaseous hydrogen chloride. Ether was added to the solution to the point of incipient precipitation, and the mixture was chilled. Thirty-four hundredths grams of crystalline trans-(±)-2-methylamino-5-n-propyl-4,4a,5,6,7,8,8a,9-octahydrothiazolo[4,5-g]-quinoline dihydrochloride were thus obtained melting above 220° C.

Analysis Calculated: C, 49.85; H, 7.17; N, 12.46; Cl, 21.02. Found: C, 49.71; H, 7.22; N, 12.31; Cl, 20.87.

Following the procedure of Example 1 but substituting N-benzylthiourea for thiourea, there was prepared trans-(±)-2-benzylamino-5-n-propyl-4,4a,5,6,7,8,8a,9-octahydrothioazolo[4,5-g]quinoline. The compound was purified by chromatography over florisil using chloroform as the eluant. The dihydrochloride salt was prepared by the above procedure. This salt was collected, dissolved in water and excess alkali added. The free base was extracted into chloroform and the chloroform removed by evaporation in vacuo to leave the free base as a residue. The maleate salt of the base was then prepared in ethanol solution, and was recrystallized from an ethanol/ether solvent mixture to yield trans-(±)-2-benzylamino-5-n-propyl-4,4a,5,6,7,8,8a,9-octahydrothiazolo[4,5-g]quinoline maleate; yield=0.17 g. (from about 10.2 millimoles of trans-(±)-1-n-propyl-6-oxo-7-bromodecahydroquinoline). The maleate melted above 210° C. and gave a single spot on TLC using the solvent system from Example 1.

Analysis Calculated: C, 63.00; H, 6.83; N, 9.18. Found: C, 63.22; H, 6.99; N, 8.95.

Other compounds according to I, III or IIIa in which R$^2$ is C$_{1-2}$ alkylphenyl are prepared in similar fashion.

Following the procedure of Example 1, 25.6 millimoles of trans-(±)-1-n-propyl-6-oxo-7-bromodecahydroquinoline were reacted with N,N-dimethylthiourea in ethanol solution. The free base of trans-(±)-2-dimethylamino-5-n-propyl-4,4a,5,6,7,8,8a,9-octahydrothiazolo[4,5-g]quinoline was obtained as a yellow viscous oil. The oil was dissolved in methanol and the methanolic solution saturated with gaseous hydrogen chloride. Ether was added to the solution to the point of incipient precipitation, and the mixture was chilled. One and twenty-five hundredths grams of a colorless solid comprising the dihydrochloride salt of trans-(±)-2-dimethylamino-5-n-propyl-4,4a,5,6,7,8,8a,9-octahydrothiazolo[4,5-g]quinoline were obtained; melting point=above 230° C.

Analysis Calculated: C, 51.13; H, 7.72; N, 11.93; Cl, 20.12. Found: C, 51.03; H, 7.46; N, 11.78; Cl, 19.83.

EXAMPLE 8

Preparation of Trans-(±)-2-methyl-5-n-propyl-4,4a,5,6,7,8,8a,9-octahydrothiazolo[4,5-g]quinoline A solution was prepared from 0.01 mole of trans-(±)-1-n-propyl-6-oxo-7-bromodecahydroquinoline hydrobromide and 35 ml. of anhydrous ethanol. Eighty-three hundredths grams of thioacetamide were added thereto and the mixture heated to reflux temperature for about 18 hours. The reaction mixture was then cooled and the cooled mixture poured into water. The aqueous mixture was made basic with concentrated aqueous ammonium hydroxide. Alkali-insoluble materials were extracted several times with chloroform. The chloroform extracts were combined and the combined extracts washed successively with water and with saturated aqueous sodium chloride and were then dried. Evaporation of the solvent in vacuo yielded in residue which was dissolved in chloroform, and the chloroform solution chromatographed over florisil using chloroform as the eluant. Fractions shown by TLC to contain trans-(±)-2-methyl-5-n-propyl-4,4a,5,6,7,8,8a,9-octahydrothiazolo[4,5-g]quinoline formed in the above reaction were combined and the solvent evaporated therefrom in vacuo. The resulting residue was dissolved in methanol, and the methanolic solution saturated with gaseous hydrogen chloride. The methanol solution was decolorized with activated charcoal and filtered. Ether was added to the filtrate to the point of incipient precipitation. Trans-(±)-2-methyl-5-n-propyl-4,4a,5,6,7,8,8a,9-octahydrothiazolo[4,5-g]quinoline dihydrochloride thus prepared was recrystallized from anhydrous ethanol to yield 0.11 g. of a colorless solid salt melting above 225° C.; $R_f$ (9:1 CHCl$_3$/MeOH+a trace of aqueous ammonium hydroxide)=0.9.

Analysis Calculated: C, 52.01; H, 7.48; N, 8.66. Found: C, 51.98; H, 7.28; N, 8.77.

EXAMPLE 9

Preparation of Trans-(±)-2-amino-4,4a,5,6,7,8,8a9-octahydrothiazolo[4,5-g]quinoline Four grams of trans-(±)-1-cyano-6-oxodecahydroquinoline prepared according to the procedure of Example 1, U.S. Pat. No. 4,198,395, were dissolved in 20 ml. of chloroform to which was added, in dropwise fashion, a solution of 1.44 ml. of bromine in chloroform. The reaction mixture was illuminated with a sunlamp as in Example 1. A colorless solid formed as the reaction progressed. After all the bromine had been added and the bromine color discharged, the solvent was removed in vacuo. The residue, comprising trans-(±)-1-cyano-6-oxo-7-bromodecahydroquinoline, showed a molecular ion at 256 by mass spectrum. The material was used without further purification.

Following the procedure of Example 1, 22.5 millimole of trans-(±)-1-cyano-6-oxo-7-bromodecahydroquinoline were dissolved in 50 ml. of ethanol to which was added 28.1 millimoles of thiourea. The reaction was carried out and the product isolated by the procedure of Example 1. The production of an equivalent of H$_2$O and an equivalent of HBr during the formation of the thiazole ring provided sufficiently acidic conditions to hydrolyze the N-cyano growth. Trans-(±)-2-amino-4,4a,5,6,7,8,8a,9-octahydrothiazolo[4,5-]quinoline thus prepared had a molecular ion at 209 by mass spectrum; yield=0.6 g. The free base was triturated with acetone to yield 0.15 g. of a solid which melted above 215° C.

Analysis Calculated: C, 57.38; H, 7.22; N, 20.08. Found: C, 57.61; H, 7.46; N, 19.80.

EXAMPLE 10

Preparation of Trans-(±)-2-amino-5-methyl-4,4a,5,6,7,8,8a,9-octahydrothiazolo[4,5-g]quinoline Two grams of trans-(±)-6-oxodecahydroquinoline furnished by the procedure of Titus and Bach, in their copending application Ser. No. 535,522, filed Sept. 26, 1983, were dissolved in 75 ml. of acetone to which was added 2.71 g. of potassium carbonate and 0.9 ml. of methyl iodide. The reaction mixture was stirred at reflux temperature over the week end, and was then cooled to room temperature and diluted with water. The aqueous mixture was extracted with a 3:1 chloroform/isopropanol solvent mixture. The extracts were combined, and the combined extracts washed with saturated aqueous sodium chloride and then dried. The solvent was removed in vacuo to yield 1.8 g. of a yellow oil comprising trans-(±)-1-methyl-6-oxodecahydroquinoline formed in the above reaction. The oil was dissolved in chloroform and the chloroform solution chromatographed over florisil using chloroform containing increasing amounts (0-4%) methanol as the eluant. Fractions shown by TLC to contain the N-methyl derivative were combined to yield 1.6 g. (73.1% yield) of a colorless viscous oil comprising trans-(±)-1-methyl-6-oxodecahydroquinoline; mass spectrum=167 (M+); single spot by TLC.

The above material (1.6 g.) was dissolved in 20 ml. of glacial acetic acid. 2.3 ml. of a 31% hydrogen bromide solution in glacial acetic acid was added followed by the dropwise addition of 0.8 ml. of bromine in 5 ml. of acetic acid. The reaction mixture was stirred at ambient temperature under ultra-violet illumination for one-half hour after which time the solvent was removed in vacuo, leaving as a residue trans-(±)-1-methyl-6-oxo-7-bromodecahydroquinoline hydrobromide.

About 10.8 millimole of the above hydrobromide salt were dissolved in 30 ml. of anhydrous ethanol to which had been added 1.03 g. of thiourea. The reaction was carried out and the product isolated according to the procedure of Example 1. Trans-(±)-2-amino-5-methyl-4,4a,5,6,7,8,8a,9-octahydrothiazolo[4,5-g]quinoline, dihydrobromide salt thus prepared was twice crystallized from methanol to yield 0.61 g. of a colorless crystalline solid melting above 235° C. TLC using 4:1 chloroform-methanol with a trace of aqueous ammonium hydroxide as the solvent system gave a single spot; $R_f$=0.30.

Analysis Calculated: C, 34.30; H, 4.97; N, 10.91; Br, 41.49. Found: C, 34.58; H, 5.21; N, 10.67; Br, 41.30.

EXAMPLE 11

Preparation of 4aS,8aS-2-Amino-5-n-propyl-4,4a,5,6,7,8,8a,9-octahydrothiazolo[3,4-g]quinoline A solution was prepared from 1.95 g. of 4aS,8aS-1-n-propyl-6-oxodecahydroquinoline in 25 ml. of glacial acetic acid. Two and three tenths milliliters of 31% hydrogen bromide in glacial acetic acid followed by 0.6 ml. of bromine in 5 ml. of glacial acetic acid were added in dropwise fashion under illumination. The bromine color was discharged immediately. After the addition had been completed, the reaction mixture was stirred for one-half hour at ambient temperature at which time the solvent was removed in vacuo. The viscous orange residue comprising 4aS,8aS-1-n-propyl-6-oxo-7-bromodecahydroquinoline dihydrobromide, formed in the above reaction, was used as such without further purification.

The orange residue was dissolved in 30 ml. of anhydrous ethanol to which solution was added 0.84 g. of thiourea. The reaction mixture was heated to refluxing temperature for about 20 hours after which time it was cooled, and the solid which had formed separated by filtration. The filter cake was washed with ethanol and ether and was then dried. Recrystallization of the filter cake from a methanol/ether solvent mixture yielded 1.17 g. of colorless crystalline 4aS,8aS-2-amino-5-n-propyl-4,4a,5,6,7,8,8a,9-octahydrothiazolo[3,4-g]quinoline dihydrobromide melting above 200° C.; molecular ion by mass spectrum=251; $[\alpha]_D^{25}$(water)= +88.4°, $[\alpha]_{365}^{25}$(water)= +312.8°; ultraviolet spectrum (ethanol), maxima at 262 nm ($\epsilon$=5725.9), 326 nm ($\epsilon$=58.8).

Analysis Calculated: C, 37.79; H, 5.61; N, 10.17. Found: C, 37.70; H, 5.81; N, 10.13.

The 4aR,8aR-1-substituted-6-oxodecahydroquinoline used to prepare the 7-bromo starting material of Example 1 is itself prepared as follows. (The preparation of the 1-n-propyl derivative is described for purposes of exemplification only. Other 1-alkyl derivatives can be resolved in similar fashion).

Preparation 1

Ten g. of (−)-di-p-toluoyltartaric acid were dissolved in 75 ml. of warm methanol. The solution was added to a solution of 5.05 g. of trans-dl-1-n-propyl-6-oxodecahydroquinoline in 15 ml. of methanol. The reaction mixture was brought to a boil and was then allowed to cool to ambient temperature. After remaining at ambient temperature overnight, crystallization was induced by the addition of seed crystals previously obtained. The crystalline tartarate salt was isolated by filtration and the filter cake washed with methanol; yield=2.813 g. (18.7%) of a white crystalline solid comprising the (−)-di-p-toluoyltartrate of 4aR,8aR-1-n-propyl-6-oxodecahydroquinoline; $[\alpha]_D^{25°}$ = −107.49°-(MeOH, c=1). Recrystallization of the salt from methanol gave 1.943 g. of the optically pure salt, $[\alpha]_D^{25°}$ = −108.29°(MeOH, c=1). The (−)-di-p-toluoyltartrate salt thus obtained was treated with dilute aqueous sodium hydroxide and the resulting alkaline solution extracted with methylene dichloride. The methylene dichloride extract was dried and concentrated, and the solvent removed therefrom in vacuo. The resulting residue was distilled to yield a colorless oil comprising purified 4aR,8aR-1-n-propyl-6-oxodecahydroquinoline; $[\alpha]_D^{25°}$ = −88.51°(MeOH, c−1).

The 4aS, 8aS derivative can be prepared in similar fashion by reacting (+)-di-p-toluoyltartaric acid with the racemate.

The preparation of pharmaceutically-acceptable acid addition salts of the compounds of this invention, particularly the hydrohalide and maleate salts, is illustrated in the above examples. Generally speaking, a solution of an equivalent of the free base represented by I, III or IIIa in a lower alkanol is mixed with an equivalent of the acid, also in solution in a lower alkanol. The salt is recovered by evaporation of the solvent and purified by recrystallization. Alternatively, an equivalent of the free base in a nonpolar organic solvent such as ether can be mixed with an equivalent of the acid, also in ether. In this procedure, the salt is usually insoluble in the solvent system and is recovered by filtration. The compounds represented by I, III or IIIa have at least two basic amine groups, the more basic group being the octahydroquinoline ring nitrogen. Disalts can be formed with these compounds by using at least two equivalents of the acid per equivalent of base. In general, only the stronger organic and inorganic acids will form disalts; the mineral acids, toluenesulfonic acid, methanesulfonic acid etc. Dihydrochloride salts are conveniently prepared by dissolving the free base in ether, saturating the ethereal solution with gaseous HCl, and recovering the dihydrochloride salt by filtration.

As previously stated, the drugs of this invention as represented by formulas I and III above are D-2 dopamine agonists. One of such D-2 dopamine agonist activities is the inhibition of prolactin secretion, as demonstrated by the following procedure.

Adult male rats of the Sprague-Dawley strain weighing about 200 g. were housed in an air-conditioned room with controlled lighting (lights on 6 a.m.–8 p.m.) and fed lab chow and water ad libitum. Each rat received an intraperitoneal injection of 2.0 mg. of reserpine in aqueous suspension 18 hours before administration of the test drug. The purpose of the reserpine was to keep the rat prolactin levels uniformly elevated. The compound was dissolved in 10 percent ethanol, and injected intraperitoneally at doses of 0.017, 0.03, 0.17 and 0.3$\mu$ moles/kg. The compound was administered at each dose level to a group of 10 rats, and a control group of 10 intact males received an equivalent amount of 10 percent ethanol. One hour after treatment, all rats were killed by decapitation, and 150 $\mu$l aliquots of serum were assayed for prolactin.

The difference between the prolactin level of the treated rats and prolactin level of the control rats, divided by the prolactin level of the control rats, gives the percent inhibition of prolactin secretion attributable to the given dose. Inhibition percentages are given in Tables 1 and 2 below for compounds according to I or III above respectively. In the tables, columns 1 and 2 give substitution patterns for the basic structures at the head of the Table, column 3 the form (salt or free base—FB), column 4, the stereochemistry trans-($\pm$) or trans-(−) (4aR,8aR) and columns 5, 6, 7 and 8, the percent prolactin inhibition at the specified dose levels.

The compounds represented by I and III are also active by the oral route, but at higher doses.

Compounds according to I and III, dopamine D-2 agonists, have also been found to affect turning behavior in 6-hydroxydopamine-lesioned rats in a test procedure designed to uncover compounds useful for the treatment of Parkinsonism. In this test, nigroneostriatal-lesioned rats are employed, as prepared by the procedure of Ungerstedt and Arbuthnott, *Brain Res,* 24, 485 (1970). A compound having dopamine agonist activity causes the rats to turn in circles contralateral to the side of the lesion. After a latency period, which varies from compound to compound, the number of turns is counted over a 15-minute period.

Results obtained from such testing are set forth in Table 2 below. In the table, columns 1 and 2 give the substitution pattern for the compound at the head of the table, column 3, salt or free base, column 4, stereochemistry, column 5, dose administered, column 6, percent of test animals exhibiting turning behavior, and column 7, average number of turns observed in first 15 minutes after end of latency period.

TABLE 2
Turning Behaviour

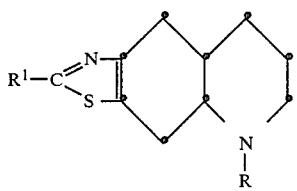

| R | R¹ | Form | Stereochemistry | dose in mcg/kg | % Rats exhibiting turning behaviour | Average No. of turns per rat |
|---|---|---|---|---|---|---|
| n-Pr | NH$_2$ | 2HBr | Trans-($\pm$) | 100 | 78 | 51 |
|  |  |  |  | 20 | 0 |  |
| " | NHCH$_3$ | 2HCl | " | 1000 | 100 | 100 |
|  |  |  |  | 100 | 100 | 80 |
|  |  |  |  | 20 | 75 | 27 |
| " | N(CH$_3$)$_2$ | " | " | 1000 | 100 | 62 |
| " | NH$_2$ | " | Trans-(−) | 1000 | 100 | 109 |
|  |  |  |  | 100 | 80 | 102 |
|  |  |  |  | 20 | 100 | 37 |
| " | 1-pyrrolidinyl | FB | Trans-($\pm$) | 1000 | 100 | 67 |
| " | NH—CO—CH$_3$ |  |  | 1000 | 100 | 91 |
| " | H | 2HCl |  | 1000 | 100 | 100 |
|  |  |  |  | 100 | 100 | 44 |
|  |  |  |  | 20 | 25 | 16 |
|  | Br | 2HCl | Trans-($\pm$) | 1000 | 100 | 42 |

TABLE 1
Percent Inhibition of Proclactin Secretion

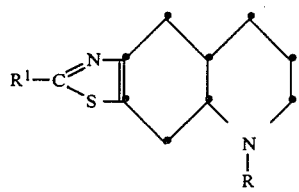

| R | R¹ | Form | Stereo-chemistry | Dose in mcg/kg |  |  |  |
|---|---|---|---|---|---|---|---|
|  |  |  |  | 100 | 50 | 10 | 5 |
| n-Pr | NH$_2$ | 2HBr | trans ($\pm$) | 93 | 88 | 60 | 35 |
| " | NHCH$_3$ | 2HCl | " | — | 82 | 62 | — |
| " | N(CH$_3$)$_2$ | " | " | — | 55 | — | — |
| " | NH$_2$ | " | trans-(−) | — | 89 | 69 | 67 |
| " | NHbenzyl | " | trans-($\pm$) | — | 67 | — | — |
| " | 1-pyrrolidinyl | maleate | " | — | 41 | — | — |
| " | NH—CO—CH$_3$ | FB | " | — | 80 | — | — |
| " | H | 2HCl | " | — | 76 | 35 | 14 |
| Me | NH$_2$ | 2HBr | " | — | 33 | — | — |
| n-Pr | H | HI methiodide | " | — | 30 | — | — |
| " | OH | HCl | " | — | 27 | — | — |

The compounds of this invention I, and III are effective in the treatment of hypertension. The compounds will demonstrate such activity in standard laboratory tests; ie., upon administration to SHR (spontaneously hypertensive rats) or in blocking NE (norepinephrine) release from sympathetic nerve terminals in pithed SHR. The compounds lack alpha adrenergic blocking activity.

Activity in affecting sexual behavior by the compounds according to I or III is demonstrated by measuring mount latency, intromission latency, ejaculatory latency, postejaculatory interval, mount frequency and intromission frequency in male rats who required at least five minutes to achieve ejaculation when a sexually receptive female is introduced into the behavioral arena prior to drug treatment. Reduction in one or more of the above indicis indicates a positive effect on sexual behaviour in male mammals including but not limited to improving potency. Sexually unresponsive male rats can also be used in such tests. Positive effects upon the sexual behaviour of female mammals are found when drugs according to I or III are administered ovariectomized, estrogen-treated female rats and the lordosis to mount ratio measured. An increase indicates a positive effect to be expected in female mammals suffering from a sexual dysfunction.

The compounds of this invention according to IIIa above are dopamine D-1 agonists. The compounds are tested for this activity by their ability to stimulate cyclic AMP formation in rat striatal membrane or in increasing cyclic AMP efflux in striatal tissue slices—see Stoof and Kebabian, *Brain Research,* 250, 263 (1982).

The compounds of this invention are usually administered for therapeutic purposes in a variety of oral formulations as illustrated below.

Hard gelatin capsules are prepared using the following ingredients:

|  | Quantity (mg./capsule) |
| --- | --- |
| Active compound | .1-2 mg |
| Starch dried | 200 |
| Magnesium stearate | 10 |

The above ingredients are mixed and filled into hard gelatin capsules.

A tablet formulation is prepared using the ingredients below:

|  | Quantity (mg./tablet) |
| --- | --- |
| Active compound | .1-2 mg |
| Cellulose, microcrystalline | 400 |
| Silicon dioxide, fumed | 10 |
| Stearic acid | 5 |

The components are blended and compressed to form tablets.

Alternatively, tablets each containing 0.1-2 mg. of active ingredient are made up as follows:
Active ingredient: 0.1-2 mg.
Starch: 45 mg.
Microcrystalline cellulose: 35 mg.
Polyvinylpyrrolidone (as 10% solution in water): 4 mg.
Sodium carboxymethyl starch: 4.5 mg.
Magnesium stearate: 0.5 mg.
Talc: 1 mg.

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°-60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed with a tablet machine to yield tablets.

Capsules each containing 0.1-2 mg. of medicament are made as follows:
Active ingredient: 0.1-2 mg.
Starch: 59 mg.
Microcrystalline cellulose: 59 mg.
Magnesium stearate: 2 mg.

The active ingredient, cellulose, starch and magnesium stearate are blended, passed through a No. 45 mesh U.S. sieve, and filled into hard gelatin capsules.

Suspensions each containing 0.1-2 mg. of medicament per 5 ml. dose are made as follows:
Active ingredient: 0.1-2 mg.
Sodium carboxymethyl cellulose: 50 mg.
Syrup: 1.25 ml.
Benzoic acid solution: 0.10 ml.
Flavor: q.v.
Color: q.v.
Purified water to: 5 ml.

The medicament is passed through a No. 45 mesh U.S. sieve and mixed with the sodium carboxymethylcellulose and syrup to form a smooth paste. The benzoic acid solution, flavor and color are diluted with some of the water and added with stirring. Sufficient water is then added to produce the required volume.

For oral administration, for treating sexual dysfunction, improving potency, lowering blood pressure (either thru a D-2 or D-1 mechanism), for increasing renal vascular flow, treating depression or anxiety, alleviating the symptoms of Parkinsonism or inhibiting prolactin release, tablets, capsules or suspensions containing from about 0.1 to about 2 mg. of active drug per dose are given 3-4 times a day, giving a daily dosage of 0.3 to 8 mgs. or, for a 75 kg. person, about 2.25 to about 600 mg./per day. The intravenous dose is in the range from about 0.1 to about 100 mcg./kg.

We claim:

1. A trans-(±)-racemate containing trans-(−) and trans-(+) enantiomers of the formula

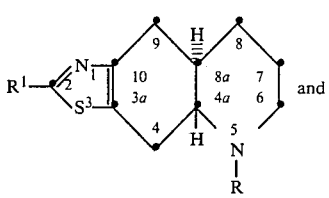

and

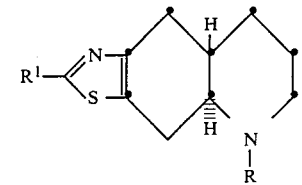

wherein R is H, $C_{1-3}$ straight-chain alkyl or allyl and $R^1$ is H, halogen, methyl, OH, $NH_2$, $NHC_{1-3}$ alkyl, $N(C_{1-3}$ alkyl$)_2$, 1-pyrrolidinyl, $NHCOC_{1-3}$ alkyl or $NHC_{1-2}$ alkylphenyl and pharmaceutically-acceptable acid addition salts thereof.

2. A trans(−) (4aR,8aR) enantiomer or a salt thereof according to claim 1.

3. A trans-(+) (4aS,8aS) enantiomer or a salt thereof according to claim 1.

4. A racemate according to claim 1 in which R is n-propyl.

5. A 4aR,8aR-enantiomer according to claim 2 in which R is n-propyl.

6. Racemates according to claim 1 in which R is $C_{1-3}$ straight-chain alkyl or allyl and $R^1$ is $NH_2$, halogen, methyl, $NHC_{1-3}$ alkyl, $N(C_{1-3}$ alkyl$)_2$, $NHCOC_{1-3}$ alkyl, 1-pyrrolidinyl or H, or acid addition salts thereof with pharmaceutically-acceptable acids.

7. A 4aR,8aR enantiomer according to claim 2 in which R is $C_{1-3}$ straight-chain alkyl or allyl and $R^1$ is $NH_2$, $NHC_{1-3}$ alkyl, $N(C_{1-3}$ alkyl$)_2$, $NHCOC_{1-3}$ alkyl, 1-pyrrolidinyl, halogen, methyl or H, or a pharmaceutically-acceptable acid addition salt thereof.

8. Racemates according to claim 6 in which $R^1$ is $NH_2$.

9. A 4aR,8aR enantiomer according to claim 7 in which $R^1$ is $NH_2$.

10. A 4aS,8aS enantiomer according to claim 3 in which $R^1$ is $NH_2$.

11. Racemates according to claim 6 in which $R^1$ is $NHCH_3$.

12. A 4aR,8aR enantiomer according to claim 7 in which $R^1$ is $NHCH_3$.

13. A hydrohalide salt of a racemate according to claim 1.

14. A hydrohalide salt of a 4aR,8aR enantiomer according to claim 2.

15. Racemates according to claim 1 in which R is H.

16. A 4aR,8aR enantiomer according to claim 2 in which R is H.

17. A racemate according to claim 1, said racemate being trans-(±)-2-amino-5-n-propyl-4,4a,5,6,7,8,8a,9-octahydrothiazolo[4,5-g]quinoline.

18. A racemate according to claim 1, said racemate being trans-(±)-5-n-propyl-4,4a,5,6,7,8,8a,9-octahydrothiazolo[4,5-g]quinoline.

19. A racemate according to claim 1, said racemate being trans-(±)-2-methylamino-5-n-propyl-4,4a,5,6,7,8-,8a,9-octahydrothiazolo[4,5-g]quinoline.

20. A racemate according to claim 1, said racemate being trans-(±)-2-acetylamino-5-n-propyl-4,4a,5,6,7,8-,8a,9-octahydrothiazolo[4,5-g]quinoline.

21. An enantiomer according to claim 2, said enantiomer being 4aR,8aR-2-amino-5-n-propyl-4,4a,5,6,7,8-,8a,9-octahydrothiazolo[4,5-g]quinoline or a pharmaceutically-acceptable acid addition salt thereof.

22. A dihydrohalide salt of the enantiomer of claim 21.

23. A trans-(±) racemate composed of enantiomers of the formulas

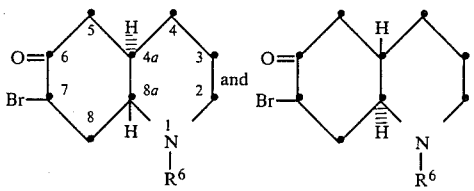

wherein $R^6$ is H, CN, benzyl, $C_{1-3}$ straight-chain alkyl or allyl and pharmaceutically acceptable acid addition salts thereof.

24. A 4aR,8aR enantiomer according to claim 23 of the formula

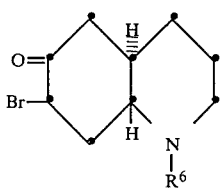

wherein $R^6$ is H, CN, benzyl, $C_{1-3}$ straight-chain alkyl or allyl.

25. A 4aS,8aS enantiomer according to claim 23 of the formula

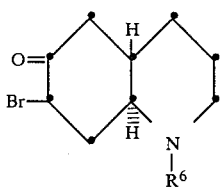

wherein $R^6$ is H, CN, benzyl, $C_{1-3}$ straight-chain alkyl or allyl.

26. An enantiomer according to claim 24, said enantiomer being 4aR,8aR-1-n-propyl-6-oxo-7-bromodecahydroquinoline.

27. A method of treating Parkinson's Syndrome consisting of administration to a mammal suffering from Parkinson's Syndrome and in need of treatment an effective dose for the treatment of Parkinson's Syndrome of a racemic drug according to claim 6.

28. A method of inhibiting the secretion of prolactin in a mammal which consists of administering to a mammal having a physiologic condition characterized in part by elevated prolactin levels and in need of treatment an amount of a racemic drug according to claim 6 effective to reduce prolactin secretion.

29. A method of treating hypertension in mammals which consist of administering to a hypertensive mammal a blood-pressure lowering dose of a racemate according to claim 6.

30. A method of treating depression in mammals which consists of administering to a mammal in a depressed state, a depression alleviating dose of a racemate according to claim 6.

31. A method of treating anxiety in mammals which consist of administering to an anxious mammal an anxiety relieving dose of a racemate according to claim 6.

32. A method for potentiating sexual behavior in mammals in need of such potentiation which comprises administering to said mammals an effective dose to potentiate sexual behavior of a trans-(±)-racemate of claim 6.

33. A method for treating sexual dysfunction in mammals suffering from such dysfunction and in need of treatment which comprises administering to said mammals an effective dose for the treatment of sexual dysfunction of a trans-(±)-racemate of claim 6.

34. A method of restoring potency in impotent male mammals in need of treatment which comprises administering to such impotent male mammals a potency restoring dose of a trans-(±)-racemate of claim 6.

35. A method of treating Parkinson's Syndrome consisting of administration to a mammal suffering from Parkinson's Syndrome and in need of treatment an effective dose for the treatment of Parkinson's Syndrome of an enantiomeric drug according to claim 7.

36. A method of inhibiting the secretion of prolactin in a mammal which consists of administering to a mammal having a physiologic condition characterized in part by elevated prolactin levels and in need of treatment, an amount of an enantiomeric drug according to claim 7 effective to reduce prolactin secretion.

37. A method of treating hypertension in mammals which consist of administering to a hypertensive mammal a blood-pressure lowering dose of an enantiomer according to claim 7.

38. A method of treating depression in mammals which consists of administering to a mammal in a depressed state, a depression alleviating dose of an enantiomer according to claim 7.

39. A method of treating anxiety in mammals which consist of administering to an anxious mammal an anxiety relieving dose of an enantiomer according to claim 7.

40. A method for potentiating sexual behavior in mammals in need of such potentiation which comprises administering to said mammals an effective dose to potentiate sexual behavior of a 4aR,8aR enantiomer of claim 7.

41. A method for treating sexual dysfunction in mammals suffering from such dysfunction and in need of treatment which comprises administering to said mammals an effective dose for the treatment of sexual dysfunction of a 4aR,8aR enantiomer of claim 7.

42. A method of restoring potency in impotent male mammals in need of treatment which comprises administering to such impotent male mammals a potency restoring dose of a 4aR,8aR enantiomer of claim 7.

43. A therapeutic process according to claim 35 in which 4aR,8aR-2-amino-5-n-propyl-4,4a,5,6,7,8,8a,9-octahydrothiazolo[4,5-g]quinoline or a pharmaceutically acceptable acid addition salt thereof is the drug used.

44. A therapeutic process according to claim 36 in which 4aR,8aR-2-amino-5-n-propyl-4,4a,5,6,7,8,8a,9-octahydrothiazolo[4,5-g]quinoline or a pharmaceutically acceptable acid addition salt thereof is the drug used.

45. A therapeutic process according to claim 37 in which 4aR,8aR-2-amino-5-n-propyl-4,4a,5,6,7,8,8a,9-octahydrothiazolo[4,5-g]quinoline or a pharmaceutically acceptable acid addition salt thereof is the drug used.

46. A therapeutic process according to claim 38 in which 4aR,8aR-2-amino-5-n-propyl-4,4a,5,6,7,8,8a,9-octahydrothiazolo[4,5-g]quinoline or a pharmaceutically acceptable acid addition salt thereof is the drug used.

47. A therapeutic process according to claim 39 in which 4aR,8-aR-2-amino-5-n-propyl-4,4a,5,6,7,8,8a,9-octahydrothiazolo[4,5-g]quinoline or a pharmaceutically acceptable acid addition salt thereof is the drug used.

48. A therapeutic process according to claim 40 in which 4aR,8aR-2-amino-5-n-propyl-4,4a,5,6,7,8,8a,9-octahydrothiazolo[4,5-g]quinoline or a pharmaceutically acceptable acid addition salt thereof is the drug used.

49. A therapeutic process according to claim 41 in which 4aR,8aR-2-amino-5-n-propyl-4,4a,5,6,7,8,8a,9-octahydrothiazolo[4,5-g]quinoline or a pharmaceutically acceptable acid addition salt thereof is the drug used.

50. A therapeutic process according to claim 42 in which 4aR,8aR-2-amino-5-n-propyl-4,4a,5,6,7,8,8a,9-octahydrothiazolo[4,5-g]quinoline or a pharmaceutically acceptable acid addition salt thereof is the drug used.

51. A pharmaceutical formulation in unit dosage form adapted for administration to counter depression, alleviate anxiety, reduce elevated blood pressure, lower excessively high prolactin levels, treat Parkinson's Syndrome, potentiate sexual behaviour, treat sexual dysfunction or restore sexual potency comprising per dosage unit, a standard pharmaceutical excipient plus an amount of a drug according to claim 6 to inhibit the secretion of prolactin, to relieve anxiety, to counter depression, to lower blood pressure of hypertensives, to treat Parkinson's Syndrome, to potentiate sexual behaviour, to treat sexual dysfunction or to restore sexual potency.

52. A pharmaceutical formulation in unit dosage form adapted for administration to counter depression, alleviate anxiety, reduce elevated blood pressure, lower excessively high prolactin levels, treat Parkinson's Syndrom, potentiate sexual behaviour, treat sexual dysfunction or restore sexual potency comprising per dosage unit, a standard pharmaceutical excipient plus an amount of a drug according to claim 7 to inhibit the secretion of prolactin, to relieve anxiety, to counter depression, to lower blood pressure of hypertensives to treat Parkinson's Syndrome, to potentiate sexual behaviour, to treat sexual dysfunction or to restore sexual potency.

53. A formulation according to claim 52 in which 4aR,8aR-2-amino-5-n-propyl-4,4a,5,6,7,8,8a,9-octahydrothiazolo[4,5-g]quinoline or a pharmaceutically-acceptable acid addition salt thereof is the active D-2 agonist.

* * * * *